(12) United States Patent
Zeitler et al.

(10) Patent No.: US 7,423,183 B2
(45) Date of Patent: Sep. 9, 2008

(54) OXIDATION OF MERCAPTOETHANOL

(75) Inventors: Michael Zeitler, Alfter (DE); Nils Kottner, Greiz (DE); Manfred Bergfeld, Erlenbach-Mechenhard (DE)

(73) Assignee: Thioplast Chemicals GmbH & Co. KG, Greiz (DE)

( * ) Notice: Subject to any disclaimer, the term of this patent is extended or adjusted under 35 U.S.C. 154(b) by 0 days.

(21) Appl. No.: 10/558,162

(22) PCT Filed: Mar. 31, 2004

(86) PCT No.: PCT/EP2004/003383

§ 371 (c)(1),
(2), (4) Date: Feb. 24, 2006

(87) PCT Pub. No.: WO2004/103956

PCT Pub. Date: Dec. 2, 2004

(65) Prior Publication Data

US 2006/0142616 A1 Jun. 29, 2006

(30) Foreign Application Priority Data

May 23, 2003 (DE) .................. 103 23 839

(51) Int. Cl.
*C07C 319/00* (2006.01)
*C07C 321/00* (2006.01)
*C07C 323/00* (2006.01)
*C07C 381/00* (2006.01)

(52) U.S. Cl. .................................... 568/59

(58) Field of Classification Search ............... 568/59
See application file for complete search history.

(56) References Cited

U.S. PATENT DOCUMENTS

| 2,792,334 | A | * | 5/1957 | Meguerian et al. ......... 208/191 |
| 3,978,137 | A | | 8/1976 | Frame |
| 4,078,992 | A | | 3/1978 | Douglas |
| 4,090,954 | A | | 5/1978 | Ward |
| 4,258,212 | A | | 3/1981 | Schenk |
| 4,288,627 | A | | 9/1981 | Kubicek |
| 4,721,813 | A | * | 1/1988 | Mark et al. .................. 568/22 |
| 6,051,740 | A | * | 4/2000 | Matson et al. ............... 568/59 |

FOREIGN PATENT DOCUMENTS

| EP | 0 288 104 | * | 10/1988 |
| EP | 0 288 104 A1 | | 10/1988 |

OTHER PUBLICATIONS

Choi et al., Synthesis of Disulfides by Copper-Catalyzed Disproportionation of Thiols, J. Org. Chem.; 1995; 60(11); 3266-3267.*
Choi, J. et al., "Synthesis of Disulfides by Copper-Catalyzed Disproportionation of Thiols," *J. Org. Chem.*, 60:3266-3267 (1995).

* cited by examiner

*Primary Examiner*—Yvonne Eyler
*Assistant Examiner*—Chukwuma O Nwaonicha
(74) *Attorney, Agent, or Firm*—Kenyon & Kenyon LLP

(57) ABSTRACT

A process for preparing dihydroxyethylene disulfide by reacting mercaptoethanol with oxygen, in which mercaptoethanol is reacted with oxygen or an oxygenous gas in the presence of ammonia and/or amines using copper salts or manganese salts.

18 Claims, 1 Drawing Sheet

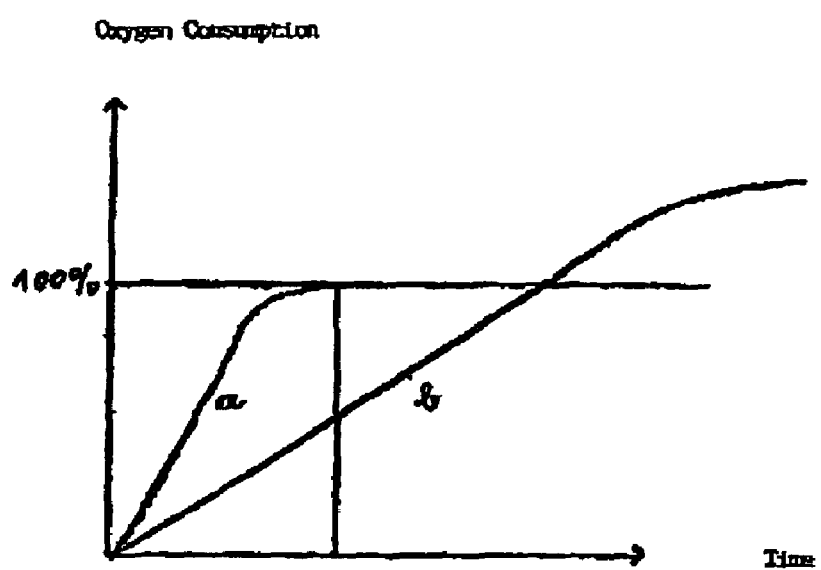
Fig I

OXIDATION OF MERCAPTOETHANOL

RELATED APPLICATIONS

This application is the U.S. National Stage of International Application No. PCT/EP2004/003383, filed Mar. 31, 2004, published in German, and claims priority under 35 U.S.C. §119 or 365 to German Application No. 103 23 839, filed May 23, 2003.

DESCRIPTION

The invention relates to a process for preparing dithiodiglycol by reacting mercaptoethanol with oxygen or oxygenous gases.

The preparation of dithiodiglycol, also known as dihydroxyethylene disulfide, can be represented by the following reaction equation.

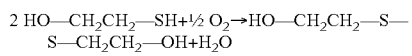

Oxidation reactions of this type have already been known for some time. For instance, U.S. Pat. No. 3,978,137 describes a process for oxidizing a sulfur-containing compound, in which this compound is reacted with an oxygen-containing gas in a medium which has a pH in the range from 8 to 14. In this reaction, a catalyst system is used which comprises VII B metal phthalocyanines and VIII metal phthalocyanines.

It can be discerned from the examples that sulfides such as sodium sulfide, ammonium sulfide, but also thiophenol and methyl mercaptan, can be reacted here.

Mercaptans with additional functional groups, for example mercaptoethanol and cysteine are also mentioned generally within a long list in the description. However, specific information on the preparation of dithiodiglycol from mercaptoethanol cannot be found in this patent.

When experiments on the preparation of dithiodiglycol by oxidation of mercaptoethanol are carried out according to the process described in this US patent, very long reaction times are firstly needed, and the yields of dithiodiglycol are secondly very low.

In addition, owing to side reactions (overoxidation), a non-uniform product is formed and has to be purified in a costly and inconvenient manner. The catalyst system used is also very complicated, costly, and expensive to prepare and remove.

The process, described in U.S. Pat. No. 4,090,954, for oxidizing mercaptans works with specific, very complicated catalysts, specifically metal complexes based on porphyrin, and is little suited to the preparation of dithiodiglycol. The complex metal used may be a wide variety of metals; however, simple metal salts as a catalyst are not mentioned. Moreover, this patent does not explicitly mention the oxidation of mercaptoethanol to dihydroxyethylene disulfide.

U.S. Pat. No. 4,258,212 describes a process for oxidizing 2-mercaptoethanol in which hydrogen peroxide is used as the oxidizing agent, but this forms a mixture of di- and trisulfides. Moreover, hydrogen peroxide is required in superstoichiometric amounts, which makes the process considerably more expensive.

U.S. Pat. No. 4,288,627 describes a process for preparing disulfides by means of oxidation of thiols, in which a catalyst mixture of cobalt molybdate and liquid tertiary amines is used. The preparation of dithiodiglycol is not described in this patent. The process applied to the preparation of dithiodiglycol works with low selectivity and with low yield, since it likewise leads to byproducts and overoxidation.

U.S. Pat. No. 4,078,992 likewise describes a process in which mercaptan-containing hydrocarbon distillates are oxidized with oxygen or an oxygen-containing gas; the catalyst used is a metal phthalocyanine.

In addition to the catalysts described there, it is also possible in the reaction to use a promoter, for example boric acid, ammonium chromate, ammonium chloride and also a metal salt, specifically iron(III) chloride. Further metal salts as promoters are not mentioned there explicitly.

Finally, reference is made to U.S. Pat. No. 4,721,813, which describes the preparation of disulfides from the corresponding mercaptoalkanols by oxidation with oxygen. This patent prescribes the use of anhydrous gaseous ammonia in small amounts, specifically in a molar ratio of ammonia to mercaptoalkanol of below 0.01:1. It is also prescribed that it is obligatory to work in the absence of any metal-containing catalysts. Although a hundred-percent conversion is stated, a comparatively high pressure is required for this purpose. The resulting product is, though, not odor-free, and there is also a very slight risk of overoxidation.

FIG. 1 compares the profile of an oxidation of mercaptoethanol according to the process of U.S. Pat. No. 4,721,813 (curve b) schematically with the profile of the oxidation of mercaptoethanol according to the invention (curve a). Curve a shows that, at 100% according to a theoretical consumption in the reaction equation specified at the outset, no further oxygen is take up, i.e. the reaction has ended and no further oxidation reactions such as overoxidation take place.

Curve b shows that, even after consumption of 100% of the theoretical amount of oxygen, further oxygen is converted, which means that additional reactions such as overoxidation take place. It has been found that secondary reactions also already proceed before the theoretical amount of 100% of oxygen has been consumed, i.e. some of the oxygen does not react according to the reaction equation specified at the outset. Overoxidation becomes noticeable by formation of compounds having a higher valence of sulfur or S—O bonds.

Even though a series of processes by which dithiodiglycol is obtainable by oxidation of mercaptoethanol is already known, there is still a great need for improved, industrially readily realizable, environmentally friendly and inexpensive processes for preparing dithiodiglycol by reacting mercaptoethanol.

It is therefore an object of the invention to provide a process which is simple to carry out, which leads to a uniform product with defined composition, which works with high yield and high selectivity and which can be carried out within short reaction times.

It is a further object of the invention to provide a process which can be carried out economically and in particular does not entail any problems for waste air and waste water, and in which there is no risk of overoxidation, even when an oversupply of oxygen or oxygenous gas is present.

This object is achieved by a process for preparing dithiodiglycol by reacting mercaptoethanol with oxygen or oxygenous gases, in which mercaptoethanol is reacted with oxygen or oxygenous gases in the presence of ammonia and/or amines using copper salts or manganese salts.

The catalysts used are preferably copper(II) or manganese (II) salts. A particular suitable copper(II) salt is copper acetate and a particularly suitable manganese(II) salt is manganese acetate.

It is advantageous to use ammonia in the form of aqueous ammonia. Amines are preferably used in anhydrous form.

Preference is given to carrying out the reaction at 20-70° C., in particular at 35-45° C.

It is advantageous in the reaction to initially charge mercaptoethanol and to meter oxygen into the initial charge.

It is also advantageous to carry out the reaction under a partial oxygen pressure of 0.5-5 bar.

Preference is given to carrying out the reaction under an elevated oxygen pressure, in particular at an elevated pressure of from 1 to 5 bar, in particular 1-2.5 bar.

It is advantageous to carry out the reaction under a constant elevated oxygen pressure.

It is advantageous to carry out the process without additional organic solvent.

In an advantageous embodiment of the process according to the invention, the reaction is carried out in aqueous medium. In the context of the invention, aqueous medium means that water is present in amounts which range from a few percent up to, for example, 70% or more, based on the total amount of substances used.

It is advantageous when the water is present in amounts of from 10 to 70% by weight.

It is possible, for example, to initially charge the water, then to add mercaptoethanol, to admix with the catalysts and also ammonia or amines, and then to introduce the oxygen or an oxygenous gas into the reactor.

It is also possible first to dissolve mercaptoethanol directly in water and to feed the solution to the reaction vessel.

The additional use of water makes it possible to control the rate of the reaction without adversely affecting the yield and selectivity. This also controls the amount of heat released per unit time, and can allow an excessively rapid rise in the temperature or an excessively vigorous reaction to be prevented.

The procedures with oxygen together with inert gases and/or in aqueous medium additionally has safety advantages. This is because possible explosion risks, which can occur, for example, in the event of sudden appearance of an ignition source, are avoided.

The process according to the invention can, for example, be carried out as follows.

A pressure reactor is initially charged with mercaptoethanol which is admixed with catalytic amounts of aqueous concentrated ammonia and also catalytic amounts of manganese salts, preferably manganese acetate or corresponding catalytic amounts of a copper salt, especially copper acetate.

Subsequently, oxygen is introduced under pressure, for example at 2.5 bar, with vigorous stirring. In the course of this, the reactor is cooled. Instead of pure oxygen, it is also possible to use an oxygenous gas mixture, for example air or oxygen, and one or more inert gases such as nitrogen or noble gases.

In order to obtain an appropriate oxygen pressure, it will be appreciated that it is necessary to adjust the total pressure in such a way that the desired partial oxygen pressure is attained.

Preference is given to adding the metal salt dissolved in ammonia or the in the amine.

In order to achieve a comparable reaction rate to that when working with pure oxygen, it is of course necessary in the case of use of oxygenous gas mixture to increase the total pressure of the gas mixture appropriately, so that the partial oxygen pressure corresponds to the pressure of oxygen in the procedure with pure oxygen.

The reaction starts up immediately. If possible, the temperature should not rise above 50° C. The reaction is strongly exothermic; therefore, it is appropriate to ensure appropriate efficient cooling. Should the temperature nevertheless rise above 50° C., the reaction can be slowed by lowering the partial oxygen pressure.

The oxygen can be introduced directly into the mercaptoethanol, and is immediately distributed within the liquid and reacts. However, it is also possible to introduce the oxygen above the liquid surface, so that an oxygen atmosphere is effectively formed above the mercaptoethanol. During the stirring (preferably with a sparging stirrer), the mercaptoethanol absorbs the oxygen required rapidly from the atmosphere.

The reaction has ended when the exact stoichiometric amount of oxygen has been consumed, which is shown by no further oxygen being absorbed from the reaction mixture.

Preference is given to carrying out the reaction under a constant elevated oxygen pressure. This can be done in such a way that an oxygen atmosphere is established in a pressure reactor over the initially charged mercaptoethanol which has been provided with the catalyst and with ammonia and/or a plurality of amines, for example with an oxygenous gas mixture with a certain elevated pressure, for example 2.5 or 5 bar. The reactor is connected to an oxygen source, for example a tube equipped with a volume meter. As long as the reaction proceeds, oxygen with the selected elevated pressure is replenished through this tube. As soon as the reaction has ended, no further oxygen consumption and thus no replenishment of oxygen either takes place.

A further variant is that a certain starting elevated pressure is established in the reaction vessel and is lowered according to the reaction profile owing to consumption of oxygen. When the oxygen has attained a certain lower pressure value, the starting pressure is restored by new supply of oxygen under pressure. This is repeated until the pressure remains constant, i.e. corresponds to the starting pressure, which means that the reaction has been conducted to completion.

A further embodiment of the process according to the invention consists in introducing an inert gas, for example nitrogen, after the mercaptoethanol has been charged into the pressure reactor. Then, supply of oxygen under pressure establishes an appropriate partial oxygen pressure to bring about onset of the reaction. To complete the reaction, the stoichiometric amount of oxygen is supplied.

The reaction does not require any organic solvent, and it is also possible to work without addition of water, i.e. the ammonia required as a catalyst can also be added to the reaction mixture in gaseous form. However, the presence of water does not disrupt the reaction.

The amines used may be primary, secondary or else tertiary aliphatic amines. It is also possible to use amine mixtures.

The amines used in the context of the invention may include the following amines: monomethylamine and also di- and trimethylamine, mono-, di- and triethylamine, mono-, di- and tripropylamine, including both the corresponding n-propyl- and isopropylamines. It is also possible to use the corresponding butylamines with linear or branched butyl radical, i.e. the corresponding n-, iso- and t-butylamines, and also mixed amines, for example dimethylethylamine, methylethylamine, diethylmethylamine and the like. The use of further aliphatic amines including those having more than 4 carbon atoms is possible.

Useful copper salts are both monovalent and divalent salts of organic or inorganic acids. Examples of monovalent copper salts include copper(I) chloride, bromide, iodide. It is also possible to use copper thiocyanates, acetates, sulfides, etc. Suitable copper(II) salts are copper(II) chloride, bromide, sulfide, sulfate, nitrate, nitrite, thiocyanate, cyanide, etc.

Particularly suitable manganese salts are manganese acetate, manganese sulfate and manganese chloride, and also manganese salts with anions as have been specified above for the copper salts.

It was particularly surprising that it is possible by means of the process according to the invention to prepare dithiodiglycol by reaction of mercaptoethanol with oxygen in high yields. The conversion is virtually 100%; the product formed has a defined uniform composition and is water-clear. No side reactions take place, so that costly purification steps are dispensed with.

It is thus also unnecessary to recover unconverted starting material. The reaction time is very short. Since the disulfide cannot be purified by distillation (decomposition), this is a particular advantage.

On completion of the reaction, the amine or the ammonia used is distilled off overhead together with water of reaction formed and can be reused for the next reaction.

Since a full conversion of the starting materials used takes place in the reaction, no particular precautions for the cleaning of the waste air are required either. There are no wastewater problems.

In contrast to the prior art processes, no further reaction takes place when oxygen is present in excess, which is a further great advantage for process safety.

The metal salt catalyst which is still present in traces in the reaction product is not disruptive. The end product can thus be further processed directly.

The invention is illustrated in detail by the examples which follow:

EXAMPLE 1

A 100 l autoclave is initially charged with 55 kg of mercaptoethanol, 200 ml of concentrated ammonia and 15 mg of manganese acetate. The reactor is equipped with a cooler and a sparging stirrer. The sparging stirrer is put into operation at room temperature and oxygen is withdrawn from a reservoir vessel at 2.0 bar via a flow meter, and the valve to the autoclave is opened.

After heating to approx. 30° C., the reaction sets in, which becomes noticeable by consumption of oxygen via the flow meter and the vigorous rise in the temperature in the reactor. It is then necessary by cooling, possibly also by reducing the oxygen pressure, to ensure that the temperature if at all possible does not exceed 60° C. As soon as the stoichiometric amount of oxygen has been introduced, for which a time of 2-5 hours is required, the reaction stops of its own accord, which is recognizable by lowering of the temperature in the reactor and stopping of the gas flow in the flow meter. The oxygen connection is then broken. In the reactor, a vacuum of 50-100 mbar is applied and water is distilled off overhead together with ammonia. As the residue, 54 kg of a clear liquid remain, which corresponds to a yield of 99.5% of dithiodiglycol.

EXAMPLE 2

Analogously to Example 1, 55 kg of mercaptoethanol are initially charged together with 150 ml of triethylamine and 25 mg of copper(II) acetate, and, after the sparging stirrer is switched on, an oxygen pressure of 4 bar is injected into the reactor and then the connection to the oxygen reservoir vessel is closed again.

The reaction sets in immediately, the temperature rises up to 60° C., and the oxygen pressure in the reactor begins to decline rapidly (oxygen consumption). When the pressure in the reactor has declined to 1.5 bar (approx. 30 min), the valve to the oxygen reservoir vessel is opened again and the pressure in the reactor is thus increased to 4 bar. There is again a noticeable temperature increase to 55° C., and the pressure then declines back to 1.5 bar over the course of approx. 30 minutes.

This procedure is repeated until there is no longer any detectable pressure decline. This indicates that the reaction has gone to completion and no further oxygen consumption takes place. The workup is effected analogously to Example 1 by applying vacuum and overhead distillation of the water of reaction together with the tertiary amine. As the residue, 54.1 kg of a clear, slightly brownish (as a result of the traces of the copper salts remaining the product) liquid with a purity of 99.9% remain, which corresponds to a yield of 99.6% of dithiodiglycol.

EXAMPLE 3

An 800 liter enameled pressure reactor from Pfaudler, which is equipped with a nozzle ring, stirrer, baffles and pressure cooler, was initially charged with 440 kg of mercaptoethanol together with 1 l of tributylamine and 200 mg of manganese sulfate, and the stirrer was put into operation. At room temperature, compressed air at 10-15 bar was then introduced through the nozzle ring at the bottom of the reactor and discharged again via a non-return (elevated pressure) valve adjusted to 8-10 bar at the bottom of the pressure cooler. This consumes a portion of the oxygen content of the compressed air, which becomes noticeable by a rise in the reaction temperature in the reactor. The amount of compressed air passed through is adjusted such that the reaction temperature in the reactor does not exceed 60° C.

At the start of the reaction, the air supply should be restricted somewhat; at the end of the reaction, in contrast, the full amount of air (of the compressor) is passed through. In spite of this, the reaction temperature falls back to room temperature after approx. 8 h; the reaction has ended. After removal of water of reaction and amine, 420 kg of a clear liquid remain, corresponding to a yield of 99%. A small fraction of mercaptoethanol is discharged with the air and is recovered in the cooler receiver, so that the selectivity of the reaction is virtually quantitative.

The invention claimed is:

1. A process for preparing dihydroxyethylene disulfide by reacting mercaptoethanol with oxygen, comprising the step of reacting mercaptoethanol with oxygen or an oxygenous gas in the presence of ammonia and/or amines using copper salts or manganese salts.

2. The process as claimed in claim 1, wherein the copper salts used are copper(II) salts.

3. The process as claimed in claim 1, wherein the manganese salts used are manganese (II) salts.

4. The process as claimed in claim 2, wherein the copper (II) salt is copper acetate.

5. The process as claimed in claim 3, wherein the manganese (II) salt is manganese acetate.

6. The process as claimed in claim 1, wherein mercaptoethanol is initially charged and oxygen is metered into the initial charge.

7. The process as claimed in claim 1, wherein the reaction is carried out under a partial oxygen pressure of from 0.5 to 5 bar.

8. The process as claimed in claim 4, wherein the reaction is carried out under an elevated oxygen pressure of 1-5 bar.

9. The process as claimed in claim 8 characterized in that the reaction is carried out at a pressure of 1-2.5 bar.

10. The process as claimed in claim 4, wherein the reaction is carried out under a constant oxygen pressure.

11. The process as claimed in claim 4, wherein a stoichiometric amount of oxygen is used for the reaction.

12. The process as claimed in claim 4, wherein aqueous ammonia is used.

13. The process as claimed in claim 4, wherein the metal salt used is dissolved in ammonia or in the amine.

14. The process as claimed in claim 4, wherein the reaction is carried out at from 20 to 60° C.

15. The process as claimed in claim 14, characterized in that the reaction is carried out at from 35 to 45° C.

16. The process as claimed in claim 4, wherein the reaction is carried out in the absence of organic solvents.

17. The process as claimed in claim 4, wherein the reaction is carried out in an aqueous medium.

18. The process as claimed in claim 17, wherein the reaction is used in the presence of 10-70% by weight of water based on the total amount of the substances used.

\* \* \* \* \*